United States Patent [19]
Hearn et al.

[11] Patent Number: 6,144,208
[45] Date of Patent: Nov. 7, 2000

[54] METHOD AND APPARATUS TO IDENTIFY ASBESTOS AND ARAMID

[75] Inventors: Graham Leslie Hearn, Southampton; John A Amner, Rochford; Peter John Walker, Bergheim, all of United Kingdom

[73] Assignee: Ford Global Technologies, Inc., Dearborn, Mich.

[21] Appl. No.: 09/184,100

[22] Filed: Oct. 30, 1998

[30] Foreign Application Priority Data

Nov. 1, 1997 [GB] United Kingdom ............... 9723006

[51] Int. Cl.[7] .................................................. G01R 27/26
[52] U.S. Cl. ............................................ 324/454; 324/452
[58] Field of Search .................................. 324/454, 452, 324/71.1, 451, 457

[56] References Cited

U.S. PATENT DOCUMENTS

| | | | |
|---|---|---|---|
| 3,866,114 | 2/1975 | Johnston | 324/32 |
| 3,999,119 | 12/1976 | Bares | 324/32 |
| 4,479,090 | 10/1984 | Frater et al. | 324/454 |
| 5,341,103 | 8/1994 | Dasgupta et al. | 324/454 |
| 5,541,518 | 7/1996 | Babbitt et al. | 324/454 |
| 5,563,516 | 10/1996 | Babbitt et al. | 324/454 |
| 5,608,326 | 3/1997 | Mucci et al. | 324/454 |

FOREIGN PATENT DOCUMENTS

| | | |
|---|---|---|
| 0767374 | 4/1997 | European Pat. Off. . |
| WO94-17402 | 8/1994 | WIPO . |

*Primary Examiner*—Safet Metjahic
*Assistant Examiner*—Vincent Q. Nguyen
*Attorney, Agent, or Firm*—Damian Porcari

[57] ABSTRACT

A method for identifying and/or differentiating between asbestos materials and aramid materials comprises the steps of rubbing an area of a surface of a material (44) to be identified, with an acrylic reference material (28), measuring the polarity of the generated electrostatic charge and comparing the polarity with polarities of charge generated from surfaces of known asbestos and aramid materials.

8 Claims, 2 Drawing Sheets

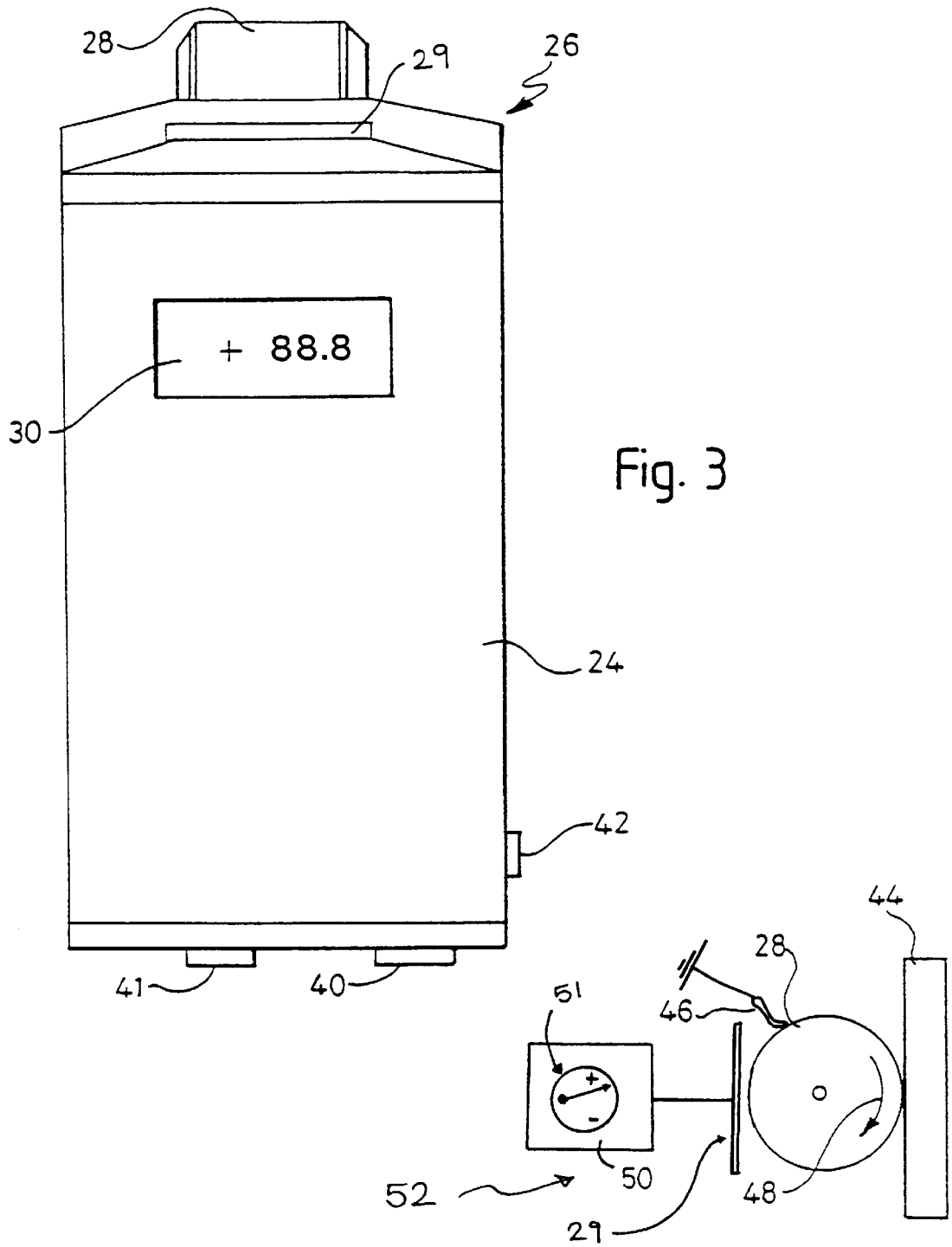

METHOD AND APPARATUS TO IDENTIFY ASBESTOS AND ARAMID

BACKGROUND OF THE INVENTION

1. Field of the Invention

The present invention relates to a method for differentiating asbestos materials from aramid materials, and to apparatus for use in performing the method. In particular, the invention relates to a method and apparatus for differentiating asbestos-based friction materials from aramid-based friction materials.

2. Description of the Related Arts

The terms "asbestos material" and "aramid material" are used herein to refer to materials which are comprised wholly or substantially of, respectively, asbestos and aramid.

Traditionally, asbestos has been used in friction materials such as vehicle brake and clutch components because of its toughness and non-flammability. In recent years, however, the use of asbestos in such applications has been restricted in many countries. Instead, an alternative material, aramid, has been increasingly used instead of asbestos. Aramid is a tough, synthetic fibrous material which is believed to be safer to health than asbestos.

Because of the restrictions with asbestos, and because of a worldwide drive to refurbish or recycle automotive components where possible, it is desirable to be able to differentiate asbestos-based materials from aramid-based materials in automotive components, notably in brake or clutch linings. Such differentiation permits disposal of each component in a suitable environmentally-friendly manner. Asbestos is invariably disposed of, but aramid fibre can be recycled.

In a known method of differentiating asbestos from aramid in an automotive component, a sample of the component is crushed into small particles and identified by viewing under a microscope. When viewed in this manner, asbestos fibres look different to aramid fibres, enabling an identification to be made. A problem with this method is that it is slow and cumbersome.

A requirement for any practical industrial method of identifying friction materials for possible recycling is that the identification is made quickly, preferably in less than one minute per sample. Slow identification speeds would slow down the rate at which components could be grouped according to material type, and this can have a significant effect on the economics of any recycling process.

SUMMARY OF THE INVENTION

According to a first aspect of the present invention, there is provided a method for identifying and/or differentiating between asbestos materials and aramid materials, the method comprising the steps of rubbing an area of a surface of a material to be identified, with an acrylic reference material, measuring the polarity of the generated electrostatic charge and comparing the polarity with polarities of charge generated from surfaces of known asbestos and aramid materials.

We found that acrylic charges positive on rubbing against aramid fibre, and weakly negative on rubbing against asbestos fibre. Thus, by determining the polarity of a friction material which is known to be either an asbestos material or an aramid material, an identification can be made.

It is preferred that asbestos and aramid materials can also be identified from other unknown materials. This can be achieved by measuring the magnitude as well as the sign of the polarity.

A triboelectric series can be derived for a particular reference material by rubbing that material with a series of other materials. If the size and polarity of the electrostatic charge thus generated is measured, the other materials can be ranked relative to each other to produce a series related to that reference material. Other series can be produced in the same way for different reference materials.

By selecting suitable reference materials, it is possible to distinguish between unknown friction materials which produce different electrostatic charges when rubbed. This does not give an absolute identification, but if the only materials expected to be present among the materials to be identified are asbestos based and aramid based friction materials, then because of the triboelectric series positions of these relative to the reference materials, it is possible to conclude that a particular sample is asbestos based and another is aramid based. In setting the invention up for use, it is first necessary to determine what materials need to be separated from one another, and then to determine the number and identity of reference materials which will achieve that separation.

A look-up table for identifying friction materials in this way can be established by recording the charge magnitude and polarity resulting from the rubbing of known friction materials against known reference materials. Once the table has been established using known samples of all the friction materials to be identified, then it can be used to identify the group to which unknown friction materials belong.

The reference materials are preferably provided in the form of rotating cylinders or discs, and the unidentified material can then be held against the cylinders whilst they rotate to produce the rubbing action. An electrostatic charge is produced as a result of this triboelectric effect. Alternatively however the rubbing action may be produced by an operator moving a reference material relative to the surface of the unidentified material, or by a combination of these two methods.

A device which uses a triboelectric effect to identify materials is known from the different technical field of plastics separation. The apparatus comprises a plastics head which is in contact with the metal head of a charge amplifier. Such apparatus is described in, for example, U.S. Pat. No. 5,608,326, WO 94/17402, EP 0 731 352, and EP 0 767 374. However, the commercially available devices presently available do not permit the reliable differentiation of asbestos and aramid.

We have surprisingly found that by mounting an acrylic head remotely from an electric field meter sensor, it is possible to differentiate the charge produced by rubbing the head with an asbestos material from the charge produced by rubbing the head with an aramid material.

Accordingly, a second aspect of the present invention provides apparatus for differentiating between asbestos materials and aramid materials, the apparatus comprising a housing provided with a reference material head of an acrylic material, means for rubbing the reference material against a sample of unidentified friction material, and a pick-up head for measuring a property of the electrostatic charge produced at the rubbing location; characterised in that the pick-up head is part of an electric field meter sensor which measures the polarity of the electrostatic charge and which is mounted remotely from the acrylic head.

Preferably the acrylic head is electrically isolated from the field meter sensor by an air gap. The most appropriate air gap will depend on the area of the acrylic head and the nature of the sensor. The air gap is preferably from 0.1 to 10 mm, notably 2 to 6 mm. In a preferred embodiment, the air gap is adjustable by translatably mounting the acrylic head and/or the pick-up plate of the electric field meter sensor in relation to the housing. This enables different field meter sensors to be used and/or other different materials to be differentiated.

Alternatively, or additionally, other materials may be provided between the surface of the acrylic head which is to carry charge, and pick-up plate of the field sensor, provided that no electrical contact is made between the two.

By taking into account merely the polarity of the electrostatic charge produced, one reference acrylic material applied to the same unknown friction material can produce a yes/no result to sort out the unknown material into two groups: asbestos materials and aramid materials. The electric field meter sensor can also measure charge magnitude, and this measurement may, if desired, be used to differentiate other materials from asbestos and aramid.

The reference acrylic material can conveniently be in the form of a cylindrical body journalled in the housing and drivingly connected to a common drive motor for rotation about an axis.

To enable the head to make contact with a sufficient area of asbestos or aramid fibre it is preferred that the head has a working surface area in the range 10 to 50 $cm^2$, notably 20 to 40 $cm^2$.

The cylindrical body can have a portion of its periphery presented to a single plane which defines a sample contact face, and the body can be carried in the housing on bearings which can be resiliently displaced from the sample contact face.

The housing is preferably small enough to be held in the hand, so that it can be readily carried around and held against a friction material component to identify the material of that component. The housing may include the power source necessary to operate the apparatus and may have a display to indicate the type of material identified. Alternatively, the housing may be connected by a conductive lead to a power source and/or to a signal processor which has such a display. The display may comprise a series of lights corresponding to the number of different material groups which can be identified, with each light being labelled with the name of the corresponding material group. An additional light may be provided to denote an insufficient rubbing action, so that the operator repeats the action.

The apparatus may also include a reset facility by which any charge which may be present on the reference material is discharged, before the apparatus is used to take a reading. This discharge process can use ions or an electrically conductive brush.

The apparatus may include a component intended to periodically clean the reference material surface. This component could be incorporated in a cap intended to be placed over the reference material when the apparatus is not being used. The inner surface of the cap may be provided, for example, with a resilient conductive material which is held in compression against the rubbing surface of the acrylic head, the conductive material being connectable to earth.

BRIEF DESCRIPTION OF THE PREFERRED EMBODIMENTS

The invention will now be further described, by way of example, with reference to the accompanying drawings, in which:

FIG. 3 is a perspective view of an embodiment of an apparatus in accordance with the invention; and FIG. 4 is a diagram illustrating operation of the apparatus.

Figure 1:
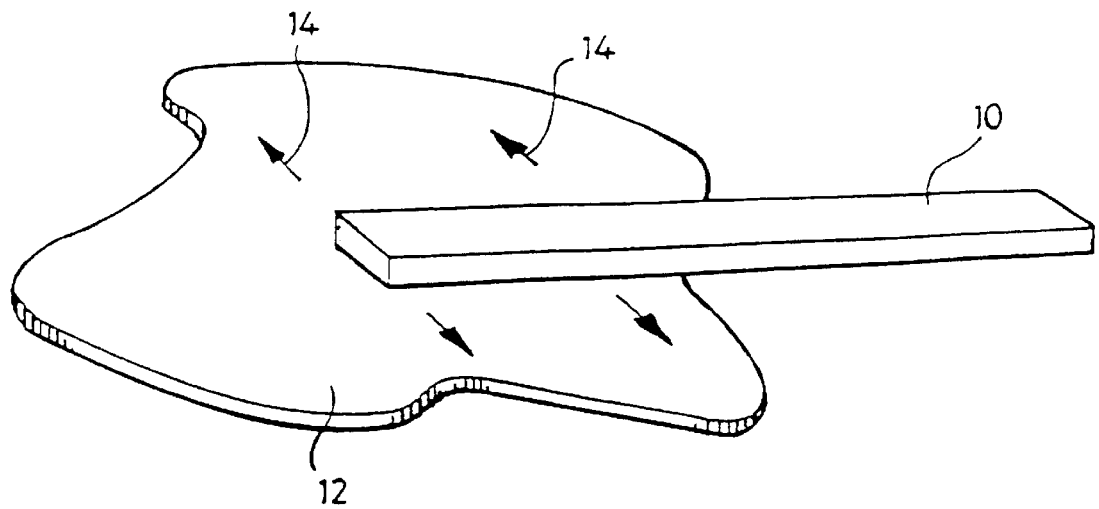
FIGS. 1 and 2 illustrate a simple electrostatic experiment on which the present invention is based.
Figure 2:
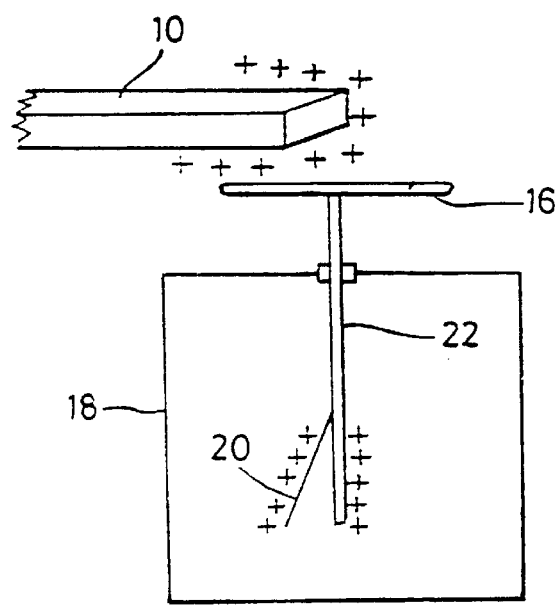

FIG. 1 shows a plastics rod 10 being rubbed over a plastics plate 12 as indicated by arrows 14. This produces an electrostatic charge on both the plate 12 and the rod 10, of equal magnitude but of opposite sign. The traditional way of demonstrating that this charge exists is to hold the end of the rod 10 close to the pick-up plate 16 of an electroscope 18. The electrostatic charge on the rod 10 causes a migration of charge in the electroscope leading to the electroscope leaf 20 being repelled from the stem 22 as a result of the repulsion effect of like electrostatic charges.

The production of an electrostatic charge in this ways is a result of the phenomenon of triboelectricity. Depending on the nature of the two materials, the charge on one will be positive and the charge on the other will be negative, or vice versa.

FIG. 3 illustrates an apparatus for doing this. The apparatus has a housing 24 of a suitable size to be held in the hand. The housing has a head unit 26 and in the head unit is a cylindrical, rotatable acrylic head 28. The housing 24 includes a drive motor (not shown) for rotating the head about its cylinder axis together with an electrostatic battery operated field meter, such as a JCI 140 static monitor, manufactured by John Chubb Instrumentation. The apparatus may be powered by batteries contained in the housing (with the batteries being recharged using a conventional battery charging device), or the apparatus may be connected by a lead (not shown) to a power source and/or to remote electronic circuitry.

The housing also incorporates an on/off switch 40, an earth connection 41 and a reset button 42.

In use, the acrylic reference head 28 is made to rub across a sample of the material being tested. This rubbing could be achieved, in the case of the rotatable body 28 by simply holding the head against a sample. However in an alternative embodiment, the head 28 could be fixed in the housing 24, and the necessary rubbing could be produced by dragging the head across the sample.

FIG. 4 illustrates operation with a driven, rotatable head 28, where the sample being tested is indicated at 44.

In use, the apparatus is switched on, so that the roller 28 starts to rotate. A surface on the sample 44 is made ready for testing by cleaning it of any dirt. It is also possible (although usually not necessary) to discharge the surface for example by wiping it with alcohol or by using some form of abrasive cleaner. The apparatus is then held against the surface to produce friction between the rotatable head 28 and the surface. As the roller 28 rotates in the direction of the arrow 48, the friction between the surface of the roller and the sample 44 produces a charge on the surface of the roller. This charge induces an equal and opposite charge on the pick-up plate 29 of the electric field meter sensor 52. The plate 29 is connected to a charge amplifier in a housing 50 provided with a meter 51. The charge (Q) on the pick-up plate 29 is developed across a capacitor in the charge amplifier and produces a voltage (V) according to the equation $Q=CV$, where C is the capacitance. The voltage is then amplified and indicated on the meter 51.

A conductive brush 46 wipes against the surface of the roller 28 remote from the sample 44 and beyond the closest point between the roller 28 and the pick-up plate 29. This charge is picked up by the brush 46 and is conducted to earth, so that after the sample 44 is removed from contact with the roller 28, charge is substantially removed from the surface of the roller.

Additionally, or alternatively, the roller 28 may be discharged by means of ions from an ion generator (not shown) actuated by pressing the reset button 42.

By measuring the polarity of the charge resulting on each reference material from the movement of that reference material against the sample, a set of results can be produced which can be compared with a stored set of results and a result can be achieved as to the type of material of the surface 44. In accordance with this result, a particular value will be displayed on the display panel 30. This value, and its sign, will be compared with known values for particular reference materials to enable the operator to identify the material of the surface 44.

If the operator does not move the apparatus across the sample correctly or for sufficient distance for an accurate reading to be obtained, then a light will light up indicating an invalid reading which should be repeated.

By operating in this way, an output is achieved which requires no previous knowledge, only a list of previously determined values, to interpret it. It would also be possible for the comparison of the value which appears on the display with a known value to be carried out electronically by the apparatus, so that the apparatus simply displays 'ASBESTOS' or 'ARAMID'. The operator can then deal with the component in accordance with that information.

The apparatus can also be provided with a cap which fits over the reference material head when the apparatus is not in use. The inside of the cap may contain cleaning and/or discharging components and the reference material may be rotated with the cap in place, to effect cleaning and/or discharging.

Alternatively cleaning and/or discharging components could be provided within the housing 24. These components could take the form of an abrasive pad and/or an alcohol swab which could be moved against the reference material head by pressing a suitably mounted lever or similar.

It will be clear to the skilled man that the housing 24 can take a wide variety of different forms. It is desirable that it should be readily portable so that it can be taken to the sample to be identified rather than vice versa. It may be necessary to periodically clean the surface of the reference material, and so a cap for the apparatus can be provided which can incorporate cleaning and discharging components.

An apparatus as described can greatly facilitate the process of recycling friction materials because it makes it possible for them to be easily identified into different families, for the appropriate recycling steps.

Although the apparatus has been described by way of example with reference to a hand held device, it is to be understood that the invention is not limited to this embodiment, and that larger devices may be constructed along the same principles set forth herein. Such devices may, for example be bench-mounted or permanently mounted alongside a conveyor belt in a breaker's yard or the like.

What is claimed:

1. A method for identifying asbestos and aramid materials, the method comprising the steps of:

rubbing an area of a surface of a material to be identified with an acrylic reference head;

measuring the polarity of a generated electrostatic charge using an electric field meter sensor electrically isolated from the acrylic reference head by an air gap; and comparing the measured polarity with polarities of charge generated from surfaces of known asbestos and aramid materials to identify the previously unidentified friction material.

2. A method as claimed in claim 1, wherein the air gap is adjustable.

3. A method as claimed in claim 1, including outputting a signal which identifies the previously unidentified friction material.

4. An apparatus for differentiating between asbestos materials and aramid materials, the apparatus comprising:

a housing provided with a reference material head of an acrylic material; and means for rubbing the reference material against a sample of unidentified friction material, and a pick-up head for measuring a property of the electrostatic charge produced at the rubbing location; characterised in that the pick-up head is part of an electric field meter sensor which measures the polarity of the electrostatic charge and which is electrically isolated from the reference material head by an air gap.

5. Apparatus as claimed in claim 4, wherein the air gap is adjustable.

6. Apparatus as claimed in claim 4, wherein the sensor is a battery operated electrostatic monitor.

7. Apparatus as claimed in claims 4, including a cap for fitting over the acrylic head, the cap being provided with a component adapted to periodically clean the acrylic reference material surface.

8. Apparatus as claimed in claim 4, wherein the acrylic head has a working area of between 10 and 50 $cm^2$.

* * * * *